United States Patent [19]

Ratajczak et al.

[11] Patent Number: 5,388,699
[45] Date of Patent: Feb. 14, 1995

[54] DUAL POCKET SPECIMEN COLLECTION PACKAGE

[75] Inventors: Janet Ratajczak, McHenry; Donald R. Harreld, Woodstock; Paul H. Hanifl, Barrington Hills, all of Ill.

[73] Assignee: Sage Products, Inc., Crystal Lake, Ill.

[21] Appl. No.: 84,856

[22] Filed: Jun. 29, 1993

[51] Int. Cl.6 .............. B65D 71/00; B65D 30/22; A61B 5/00
[52] U.S. Cl. ................ 206/569; 128/760; 206/438; 383/38; 383/63; 383/95
[58] Field of Search ............ 206/569, 568, 438; 383/37, 38, 63, 65, 95; 128/760, 771

[56] References Cited

U.S. PATENT DOCUMENTS

| | | | |
|---|---|---|---|
| 3,279,331 | 10/1966 | Platt | 383/95 X |
| 3,473,589 | 10/1969 | Götz | 383/63 X |
| 3,643,650 | 2/1972 | Elder | 206/569 X |
| 4,637,061 | 1/1987 | Riese | 383/38 |
| 4,720,040 | 1/1988 | Gurewitz | 383/38 X |
| 4,777,964 | 10/1988 | Briggs et al. | 128/760 |
| 4,927,405 | 5/1990 | Martin et al. | 383/38 X |
| 5,022,409 | 6/1991 | Goldstein et al. | 128/760 |
| 5,024,536 | 6/1991 | Hill | 383/38 |

Primary Examiner—Bryon P. Gehman
Attorney, Agent, or Firm—Lee, Mann, Smith, McWilliams, Sweeney & Ohlson

[57] ABSTRACT

A specimen collection kit particularly for collection and transport of urine specimens. The kit includes a first pouch sealed about its periphery and encapsulating a collection container therewithin. A second pouch is provided, also with a peripheral seal, and encapsulating one or more test vials for specimen testing. The second pouch also includes a resealable seal proximate one edge such that the second pouch can be resealed after opening of the peripheral seal on that edge. The pouches are united along one edge of each pouch, and a perforation is provided at that juncture to permit severing of the two pouches.

8 Claims, 1 Drawing Sheet

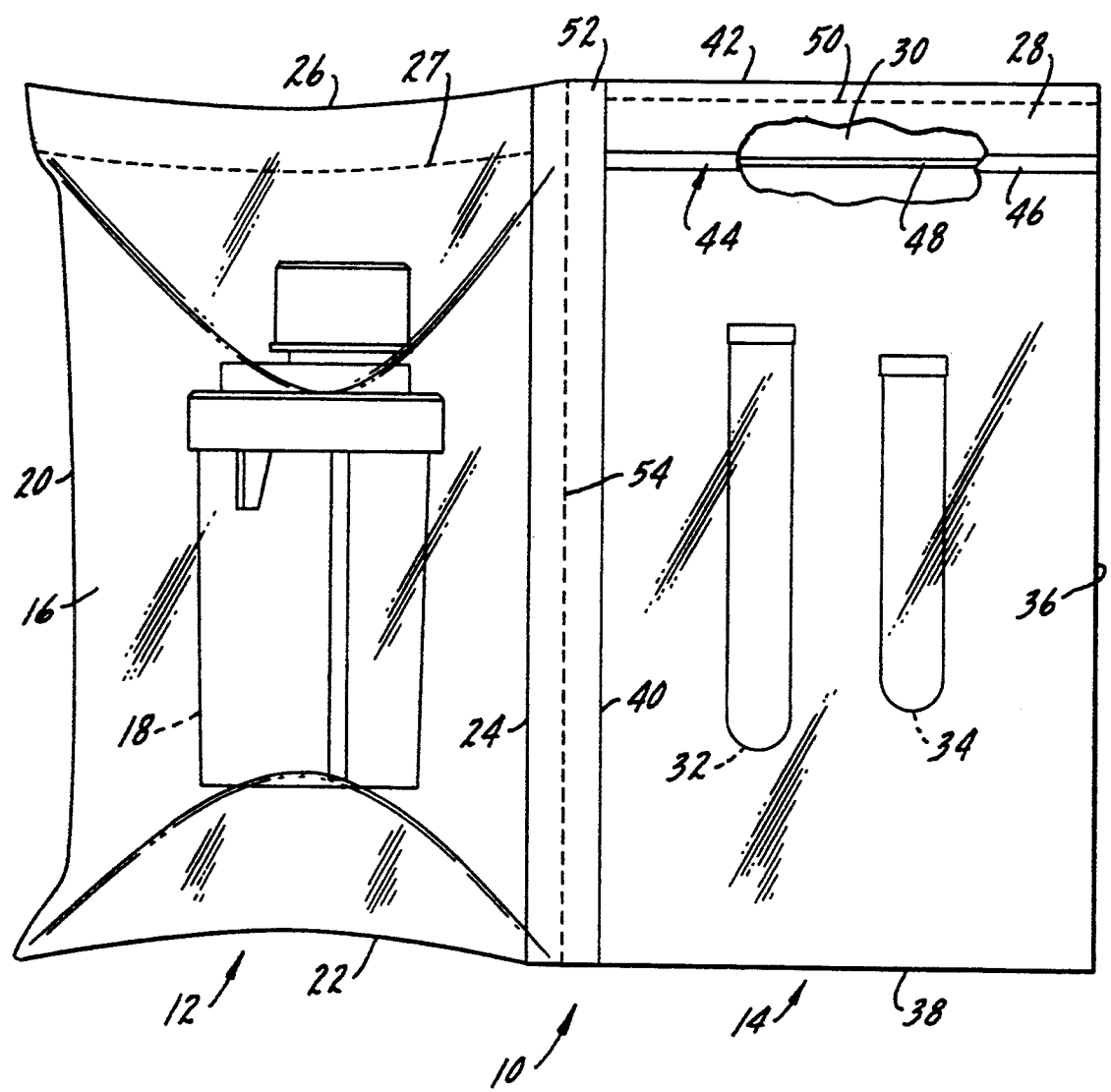

DUAL POCKET SPECIMEN COLLECTION PACKAGE

BACKGROUND OF THE INVENTION

This invention relates to specimen collection, and in particular to a specimen collection kit having multiple pouches, one of the pouches being severable from the other and being reusable after having been opened.

Specimen collection for testing of biological fluids is a necessary part of any significant test work done on any patient. In its simplest form, a specimen collector comprises a container with a removable cover. Once a sample has been collected and the cover reapplied, the specimen collector is transported to an appropriate facility where sampling takes place.

More complex sampling apparatus has also been developed. For example, U.S. Pat. No. 4,300,404 describes a liquid specimen container which has not only a receptacle for fluids, but also an integral sampling portion therein. The specimen container of this patent is normally provided with one or more air-evacuated vials which are used to collect portions of the specimen in the container. The specimen container, the vials and cleansing towelettes are all provided in a simple plastic bag for transporting of these items. Once one or more of the vials has been used to withdraw a portion of the specimen, the specimen and container is typically discarded, the vials are returned to the plastic bag, and the vials are then transported for further analysis and/or testing.

One of the problems of using a simple plastic bag is the fact that the bag cannot be resealed. Also, the bag carries the vial, the specimen container and the towelettes, and therefore is not internally sterile. It is preferable to separate the vials from the specimen container, and also provide some means of resealing the vials in their plastic bag once the specimens have been withdrawn.

SUMMARY OF THE INVENTION

The invention is directed to a specimen collection kit for collection of biological fluids. The kit includes a first pouch comprising opposite plastic sheets having a peripheral seal to encapsulate at least one container therewithin. A second pouch is provided, also comprising opposite plastic sheets having a peripheral seal to encapsulate at least one container therewithin. The second pouch also includes a resealable seal proximate one edge of the second pouch such that the second pouch is resealable by the resealable seal after opening of the peripheral seal of the second pouch adjacent the resealable seal. Means is provided for severably joining the first and second pouches.

In accordance with the preferred form of the invention, the plastic sheets of the pouches are continuous from one pouch to the other, and the means for severably joining comprises a line of weakening between adjacent peripheral seals of the pouches where the pouches are contiguous. Preferably, the line of weakening comprises a line of perforation.

The resealable seal can take on several different forms. In one form of the invention, the resealable seal comprises an adhesive seal composed of complementary adhesive strips secured to an inside surface of each of the plastic sheets of the second pouch. In another form of the invention, the resealable seal comprises an interlocking seal formed of complementary snap lock strip elements secured to the inside surfaces of the plastic sheets of the second pouch.

The peripheral seals are preferably heat seals. Thus, when a peripheral seal has been severed, it cannot be rejoined. Only the resealable seal can be rejoined to reseal the second pouch.

In accordance with the invention, a specimen collection container is encapsulated within the first pouch, while one or more diagnostic vials is encapsulated within the second pouch. A packet of cleansing towelettes can also be sealed with the specimen collection container. Once the first pouch has been opened, the specimen collection container cannot be resealed in the pouch, while opening of the second pouch adjacent the resealable seal permits samples to be inserted in the vials, and the vials then replaced in the second pouch and the pouch resealed for transport.

BRIEF DESCRIPTION OF THE DRAWING

The invention is described in greater detail in the following description of an example embodying the best mode of the invention, taken in conjunction with the single drawing FIGURE, in which is illustrated an elevational view of a specimen collection kit according to the invention, with a portion broken away in the second pouch to illustrate the resealable seal.

DESCRIPTION OF AN EXAMPLE EMBODYING THE BEST MODE OF THE INVENTION

A specimen collection kit according to the invention is designated generally at 10 in the drawing FIGURE. The specimen collection kit comprises two portions, a first pouch 12 and a second pouch 14.

The first pouch comprises opposite plastic sheets, a front sheet 16 being illustrated in the drawing FIGURE. A specimen collection container 18 is encapsulated between the sheets of the first pouch, the first pouch having peripheral heat seals 20, 22, 24 and 26 fully sealing the pouch 12 along the four sides thereof. The specimen container 18 preferably is the container described in U.S. Pat. No. 5,312,009, filed Jun. 7, 1993, and entitled "Liquid Specimen Collector with Removable Extraction Device", although other specimen collection containers could also be used with the invention. In addition to the specimen collection container 18 being sealed within the first pouch 12, other items, such as a packet of cleansing towelettes, may also be included in the pouch 12 before the heat seals 20–26 are completed. A perforation 27 or similar line of weakening may be provided in the pouch 12 to facilitate opening.

The second pouch 14 is also formed of front and rear plastic sheets 28 and 30. One or more vials 32 and 34 is inserted between the plastic sheets 28 and 30, and the plastic sheets are formed into the second pouch 14 by means of peripheral heat seals 36, 38, 40 and 42 along the edges of the second pouch 14.

The second pouch 14 also includes a resealable seal 44 extending between the opposite seals 36 and 40, and spaced inwardly a short distance from the seal 42. The resealable seal 44 comprises a seal portion 46 secured to the inside of the sheet 28, and a complementary seal portion 48 secured to the inside of the sheet 30. The seal portions 46 and 48 mate to form the resealable seal 44. The resealable seal 44 may comprise an adhesive seal, where one or both of the seal portions 46 and 48 are adhesive strips. Similarly, the resealable seal 44 may comprise an interlocking seal, with the seal portions 46 and 48 comprising complementary snap lock strip elements, such as the common ZipLok seal. Whether adhesive, interlocking or otherwise, the resealable seal 44 is formed to be severed and resealed a number of times without damage to the integrity of the seal formed thereby.

While the resealable seal 44 is shown at the top of the pouch 14, it could also be along the seal 36, extending between the seals 38 and 42, or at the bottom of the pouch. Also, to facilitate initial opening of the pouch 14, a perforation 50 may be located between the seal 42 and the resealable seal 44, as illustrated. The perforation 50 can also serve (by its severing) as evidence of tampering with the contents of the pouch 14.

It is preferred that the front sheets 16 and 28 of the two pouches 12 and 14 be a continuous plastic sheet, and likewise the rear sheets 30 of the second pouch 14 and the rear sheet of the first pouch 12 be a continuous plastic sheet. As illustrated in a somewhat exaggerated fashion in the drawing FIGURE, the heat seals 24 and 40 are spaced apart, forming a non-pouch area 52 between the two pouches 12 and 14. The specimen collection kit 10 is formed with a severable line of weakening 54 between the two pouches. Preferably, the line of weakening 54 is a perforation through the sheets of the pouches, although other types of separation can be provided so that the first and second pouches 12 and 14 may readily be severed from one another along the line 54.

In use, the specimen collection kit 10 is formed by sealing the container 18 and vials 32 and 34 (and any additional parts of the kit desired) within the respective pouches 12 and 14. Then, when a specimen is required, the nurse, doctor or technician severs the collection kit along the perforation 52, handing the first pouch 12 to the patient who removes the specimen container 18 and collects the required specimen. The pouch 12, which has been irrevocably broken open, is then discarded.

Once the sample has been collected, the container 18 is returned to the appropriate person, who opens the pouch 14 by either severing the heat seal 42 or cutting open that end of the second pouch 14 along the perforation 50, if provided. One or both of the vials 32 and 34 is removed, used for sampling of the specimen in the container 18, and then returned to the pouch 14. The resealable seal 44 is then closed, and the second pouch 14 is used for transport to a laboratory or other location for analysis of the contents of the vials 32 and/or 34. Thus, the pouch 14 not only serves as a storage pouch for the vials when the specimen collection kit 10 is complete, but also serves as a transport pouch separate from the first pouch 12 after a sample has been collected in either of the vials 32 or 34. In this manner, the vials are always sealed within the transport pouch 14, thus greatly reducing the chances of contamination.

Various changes can be made to the invention without departing from the spirit thereof or scope of the following claims.

What is claimed is:

1. A specimen collection kit comprising
   a. a first sealed pouch comprising opposite plastic sheets having a peripheral seal,
   b. a specimen collection container encapsulated within said first pouch,
   c. a second sealed pouch comprising opposite plastic sheets having a peripheral seal,
   d. at least one diagnostic vial encapsulated within said second pouch,
   e. a resealable seal in said second pouch proximate one edge of said second pouch such that said second pouch is resealable by said resealable seal after opening of the peripheral seal of the second pouch adjacent the peripheral seal, and
   f. means severably joining said first and second pouches.

2. A specimen collection kit according to claim 1 in which the plastic sheets of said pouches are continuous from one pouch to the other, and said means severably joining comprises a line of weakening between adjacent peripheral seals of said pouches.

3. A specimen collection kit according to claim 2 in which said line of weakening comprises a line of perforation.

4. A specimen collection kit according to claim 1 in which said resealable seal comprises an adhesive seal.

5. A specimen collection kit according to claim 4 in which said adhesive seal comprises an adhesive strip secured to an inside surface of at least one plastic sheet of said second pouch.

6. A specimen collection kit according to claim 1 in which said resealable seal comprises an interlocking seal.

7. A specimen collection kit according to claim 6 in which said interlocking seal comprises a complementary snap lock strip element secured to an inside surface of each plastic sheet of said second pouch.

8. A specimen collection kit according to claim 1 in which said peripheral seals are heat seals.

* * * * *